United States Patent
Kosierkiewicz

(10) Patent No.: US 10,588,539 B1
(45) Date of Patent: Mar. 17, 2020

(54) METHOD FOR A DRY ELASTOMER ELECTRODE

(71) Applicant: Tomasz Andrzej Kosierkiewicz, Mount Vernon, IL (US)

(72) Inventor: Tomasz Andrzej Kosierkiewicz, Mount Vernon, IL (US)

( * ) Notice: Subject to any disclaimer, the term of this patent is extended or adjusted under 35 U.S.C. 154(b) by 0 days.

(21) Appl. No.: 15/427,025

(22) Filed: Feb. 7, 2017

Related U.S. Application Data

(60) Division of application No. 14/019,144, filed on Sep. 5, 2013, now Pat. No. 9,586,038, which is a
(Continued)

(51) Int. Cl.
| | |
|---|---|
| *A61B 5/053* | (2006.01) |
| *A61B 5/00* | (2006.01) |
| *B29C 65/48* | (2006.01) |
| *B29C 65/00* | (2006.01) |
| *B32B 7/02* | (2019.01) |
| *B32B 7/12* | (2006.01) |
| *B32B 27/28* | (2006.01) |
| *B32B 37/10* | (2006.01) |
| *B32B 37/12* | (2006.01) |
| *B29L 31/00* | (2006.01) |
| *B29K 683/00* | (2006.01) |
| *B29K 505/14* | (2006.01) |

(52) U.S. Cl.
CPC ............ *A61B 5/053* (2013.01); *A61B 5/6832* (2013.01); *B29C 65/486* (2013.01); *B29C 65/4855* (2013.01); *B29C 66/45* (2013.01); *B29C 66/73141* (2013.01); *B32B 7/02* (2013.01); *B32B 7/12* (2013.01); *B32B 27/283* (2013.01); *B32B 37/10* (2013.01); *B32B 37/12* (2013.01); *A61B 2562/0209* (2013.01); *A61B 2562/125* (2013.01); *A61B 2562/14* (2013.01); *A61B 2562/164* (2013.01); *B29K 2505/14* (2013.01); *B29K 2683/00* (2013.01); *B29L 2031/752* (2013.01); *B29L 2031/753* (2013.01); *B32B 2255/10* (2013.01); *B32B 2305/30* (2013.01); *B32B 2307/202* (2013.01); *B32B 2383/00* (2013.01); *B32B 2535/00* (2013.01)

(58) Field of Classification Search
None
See application file for complete search history.

(56) References Cited

U.S. PATENT DOCUMENTS

| | | |
|---|---|---|
| 5,075,038 A | 12/1991 | Cole et al. |
| 5,263,481 A * | 11/1993 | Axelgaard ......... A61B 5/04085 600/384 |

(Continued)

*Primary Examiner* — Gary Jackson
*Assistant Examiner* — Elizabeth K So
(74) *Attorney, Agent, or Firm* — Loza & Loza, LLP; Jessica W. Smith

(57) ABSTRACT

An electrode with varying impedances includes a plurality of layers that are compressed together with varying compressions forces. A first compression force is used at the perimeter of the electrode and a second compression force is used towards the center of the electrode. The first compression force at the perimeter is lesser than the second compression force towards the center and creates a greater measured impedance at the perimeter of the electrode than at the center of the electrode.

20 Claims, 14 Drawing Sheets

Related U.S. Application Data continuation-in-part of application No. 13/020,392, filed on Feb. 3, 2011, now Pat. No. 8,569,935, which is a continuation-in-part of application No. 12/835,972, filed on Jul. 14, 2010, now abandoned, which is a continuation-in-part of application No. 12/559,061, filed on Sep. 14, 2009, now abandoned.

(60) Provisional application No. 61/819,574, filed on May 4, 2013, provisional application No. 61/788,575, filed on Mar. 15, 2013, provisional application No. 61/347,963, filed on May 25, 2010.

(56) References Cited

U.S. PATENT DOCUMENTS

| | | | |
|---|---|---|---|
| 5,501,764 A * | 3/1996 | Inselmann | A41H 43/04 |
| | | | 156/580 |
| 5,520,683 A * | 5/1996 | Subramaniam | A61N 1/0492 |
| | | | 606/32 |
| 6,156,236 A | 12/2000 | Hayashida et al. | |
| 6,734,250 B2 | 5/2004 | Azechi et al. | |
| 2005/0015134 A1 * | 1/2005 | Carim | A61B 5/0408 |
| | | | 607/142 |
| 2010/0000781 A1 | 1/2010 | Tanaka et al. | |
| 2014/0113433 A1 * | 4/2014 | Nguyen | H01L 21/67092 |
| | | | 438/455 |

\* cited by examiner

METHOD FOR A DRY ELASTOMER ELECTRODE

CROSS-REFERENCE TO RELATED PATENTS

This present U.S. Utility Patent Application claims priority under 35 U.S.C. 120 to U.S. patent application Ser. No. 14/019,114 (now U.S. Pat. No. 9,586,038) entitled, "SYSTEM AND METHOD FOR A DRY ELASTOMER ELECTRODE," filed Sep. 5, 2013, which:

claims priority to U.S. Provisional Application Ser. No. 61/788,575, entitled, "SYSTEM AND METHOD FOR A DRY ELASTOMER ELECTRODE," filed Mar. 15, 2013;

claims priority to U.S. Provisional Application Ser. No. 61/819,574, entitled, "SYSTEM AND METHOD FOR A DRY ELASTOMER ELECTRODE," filed May 4, 2013, all of which are incorporated by reference herein and made part of the present U.S. Utility Patent Application for all purposes; and claims priority as a continuation-in-part of U.S. application Ser. No. 13/020,392 (now U.S. Pat. No. 8,569,935), filed Feb. 3, 2011, which claims priority as a continuation-in-part of U.S. application Ser. No. 12/835,972, filed Jul. 14, 2010, now abandoned, which is a continuation-in-part of application Ser. No. 12/559,061, filed Sep. 14, 2009, now abandoned, and which claims benefit of U.S. Provisional Application Ser. No. 61/347,963, filed May 25, 2010;

all of which are incorporated by reference herein and made part of the present U.S. Utility Patent Application for all purposes.

BACKGROUND

Technical Field

This application relates generally to medical electrodes, and in particular to a low impedance dry stimulation and recording electrode with at least one layer having an elastomeric surface.

Description of Related Art

In the medical field, electrodes are utilized to establish electrical contact with the skin of a patient, and are commonly used for the administration of electrical signals to the patient as well as for receiving electrical signals generated in the body of the patient.

Contact between the electrode and the skin of the patient is typically made through the use of conductive gels, pastes or creams. The conductive gels, pastes or creams are typically applied directly to the surface of the skin of the patient. As can be appreciated, the use of these conductive products can be problematic, as they may produce bridging artifacts, may cause the electrode displacement, i.e., the electrode may slide away from the desired position, or may even dry out rendering the electrode useless and any recording impossible (pertaining mostly to prolonged intraoperative monitoring). The conductive gels, pastes or creams are messy and often irritate the skin of the patient. Another disadvantage of the conductive gels, pastes and creams is that they leave a residue on the skin of the patient subsequent to the removal of the electrode therefrom, thereby requiring additional cleaning of the patient when finished, thus extending the preparation and testing time.

Accordingly, there is a need for systems and methods for providing a dry elastomer electrode that can be utilized in the medical industry without the need for applying conductive gels, pastes or creams to the patient. Dry biocompatible elastomer electrodes are durable, and re-usable. Can be incorporated into fabrics and clothing and can be worn for long periods of time. The rubbery surface of the electrode provides a smooth and uniform contact surface with the skin. Silicon rubber traps moisture (sweat) which helps to reduce the skin-to-electrode impedance, and thereby reduces electrode susceptibility to motion artifacts and noise. On the other hand, traditional wet gel electrodes will not work on the skin of a diaphoretic patient.

BRIEF DESCRIPTION OF THE SEVERAL VIEWS OF THE DRAWINGS

FIG. 1c is an exploded top perspective view of an embodiment of a dry elastomer electrode as similarly shown in FIG. 1a;

FIG. 8b is a top view of the digital ring electrode a similarly shown in FIG. 8a;

DETAILED DESCRIPTION

Figure 1A:
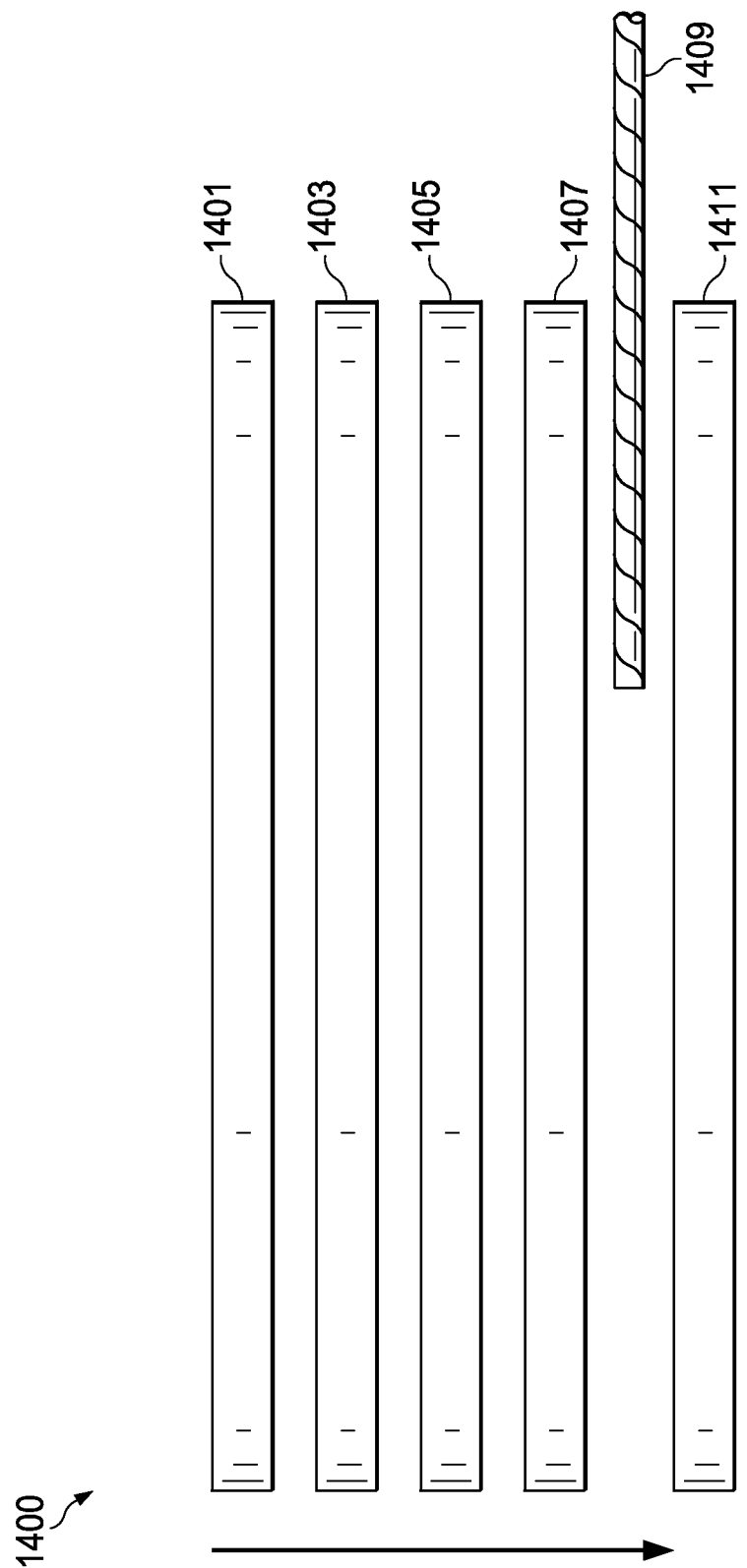
FIG. 1a is an exploded side view of an embodiment of a dry elastomer electrode.

Referring now to the figures, wherein various elements depicted therein are not necessarily drawn to scale and wherein, through various views and figures, like elements may be referenced with identical reference numerals, there are illustrated embodiments of a dry elastomer electrode.

FIGS. 1a-c and FIG. 2 illustrate embodiments of a dry elastomer electrode. The electrodes 1400 (FIGS. 1a and 1c), 1600 (FIG. 1b), and 1800 (FIG. 2) may be a transcutaneous medical electrode for stimulating nerves and/or muscles by generating electricity that could be used in different parts of the body. The electrodes 1400, 1600, and 1800 may be employed for other uses as well. In an embodiment, the electrodes 1400, 1600, and 1800 include a substantially dry body comfortable, biocompatible, electrically conductive interfacing layer of a metal-integral conductive silicon rubber sheet. The dry elastomer electrodes 1400, 1600, and 1800 are employed for similar uses as adhesive electrodes or gel electrodes or where such electrodes may not be appropriate or desirable. For example, the electrodes 1400, 1600, and 1800 may replace an adhesive electrode, e.g. where allergic reaction may be possible.

Figure 1B:
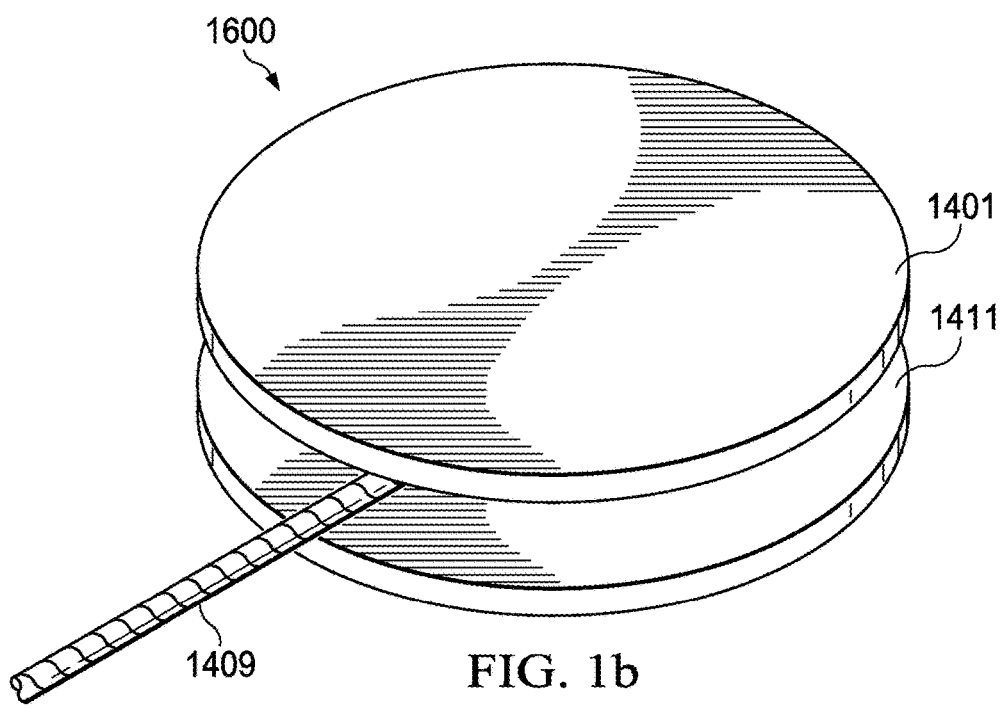
FIG. 1b is an exploded top perspective view of another embodiment of a dry elastomer electrode.
Figure 1C:
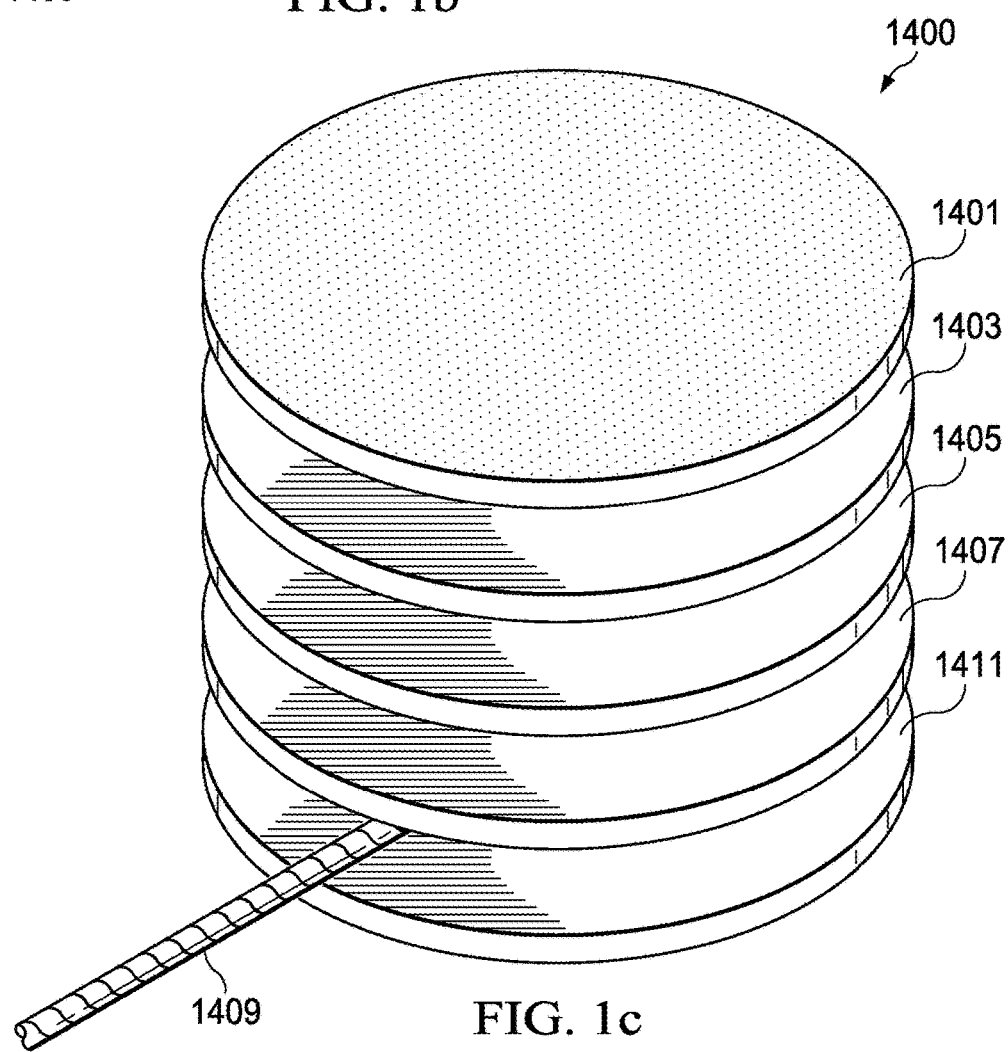

FIGS. 1a and 1c illustrate the electrode 1400 which includes in an embodiment at least an upper/first sheet 1401 of metal integral conductive silicon rubber (or elastomer) which, by way of example and not limitation, may be a gold, silver, silver plated copper, or other conductive metal plated material filled silicon. Electrode 1400 further includes a second layer 1403 which may be a conductive adhesive gel layer to adhere to the first sheet 1403, a third sheet 1405 of a conductive carbon film to adhere to the second layer 1403, and a fourth sheet 1407 which may be a conductive metal sheet and the metal may be silver or other appropriate metals. An electrical lead 1409 is positioned and secured between the fourth sheet 1407 and the fifth sheet 1411. The electrical lead 1409 facilitates the delivery of energy to the electrode 1400 from a power source (not shown). Fifth sheet 1411 may be a dielectric/non-conducting flexible backing sheet.

FIG. 1b illustrates the electrode 1600 which includes two layers 1401 and 1411. Electrode 1600 includes an upper/first sheet 1401 of metal integral conductive silicon rubber (or elastomer) which, by way of example and not limitation, may be a gold, silver, silver plated copper, or other conductive metal plated material filled silicon. Electrode 1600 further includes an electrical lead 1409 which is positioned and secured between the first sheet 1401 and the bottom sheet 1411. The electrical lead 1409 facilitates the delivery of energy to the electrode 1600 from a power/recording source (not shown). The bottom sheet 1411 may be a dielectric/non-conducting flexible backing sheet.

Figure 2:
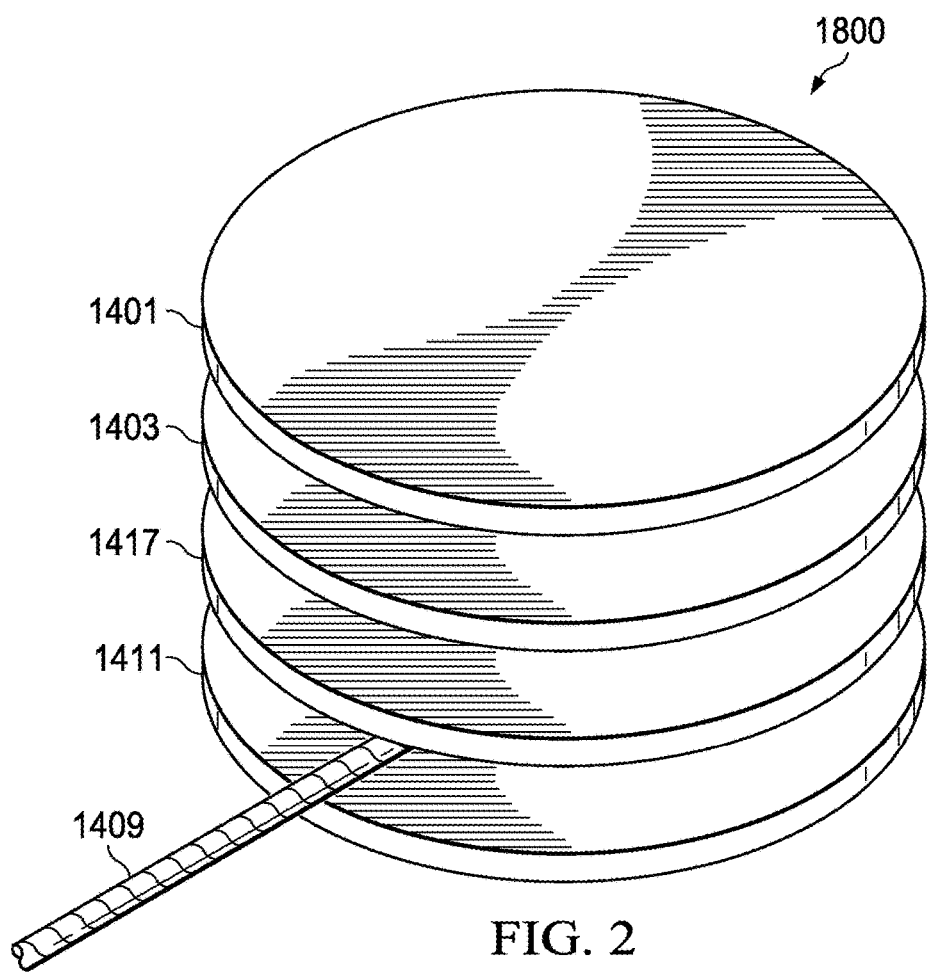
FIG. 2 in an exploded top perspective view of another embodiment of a dry elastomer electrode.
Figure 3:
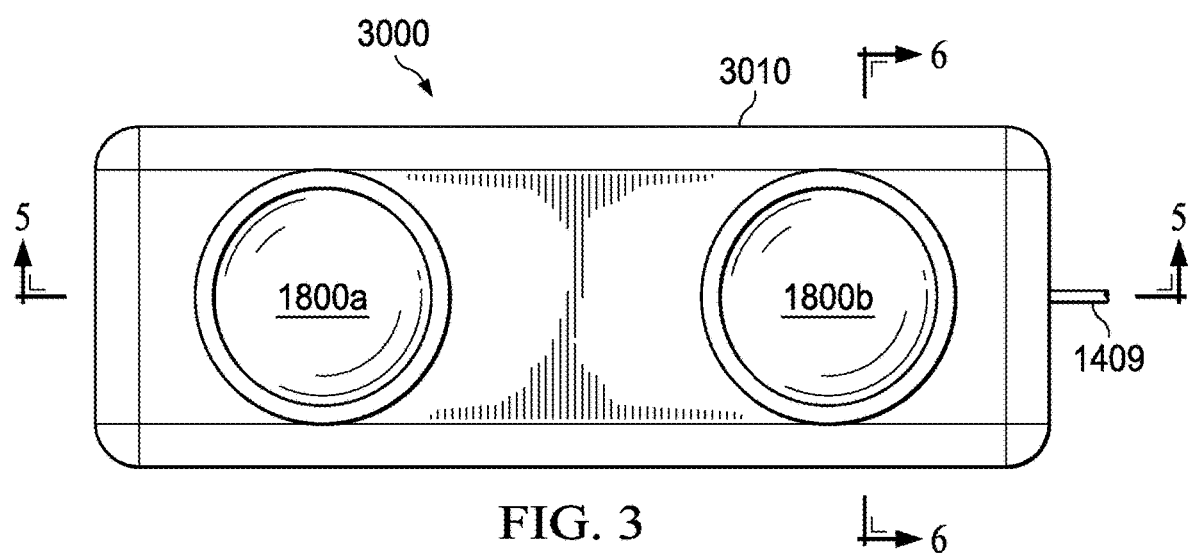
FIG. 3 is a top view of an embodiment of a dry elastomer electrode in a bar electrode.
Figure 4:
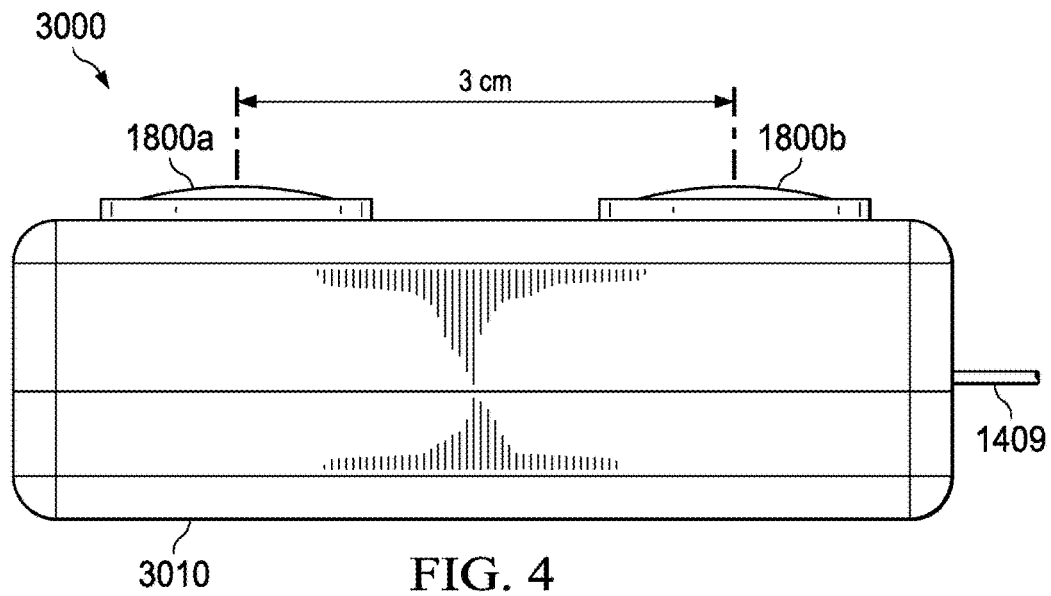
FIG. 4 is a side view of an embodiment of a dry elastomer electrode in a bar electrode as similarly shown in FIG. 3.
Figure 5:
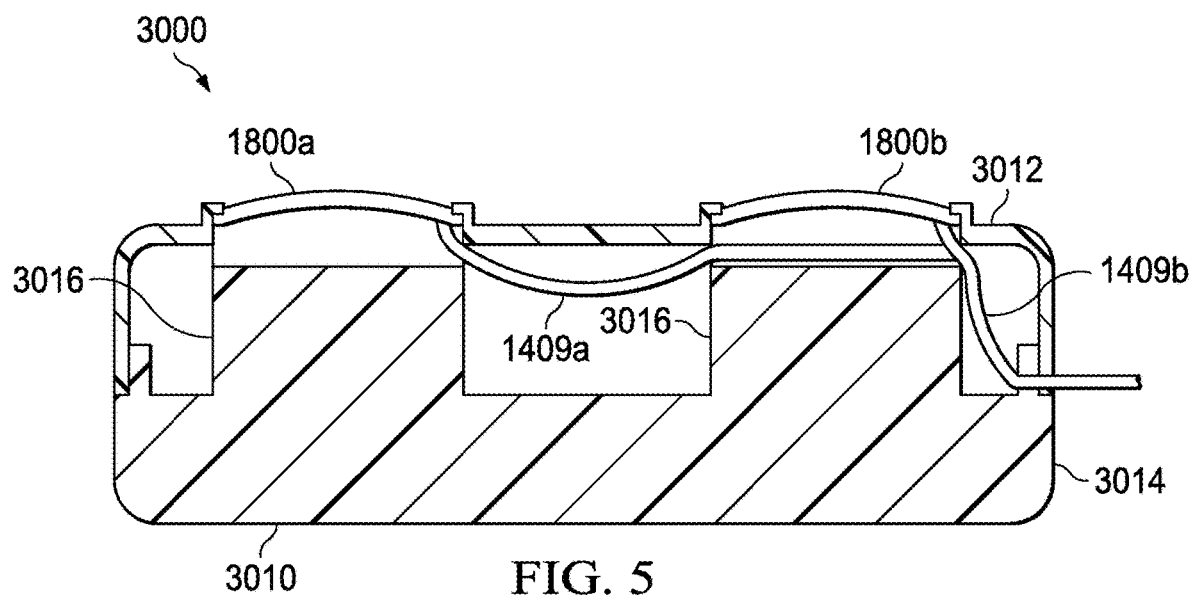
FIG. 5 is a cross-sectional side view taken along line 5-5 of FIG. 3.
Figure 5A:
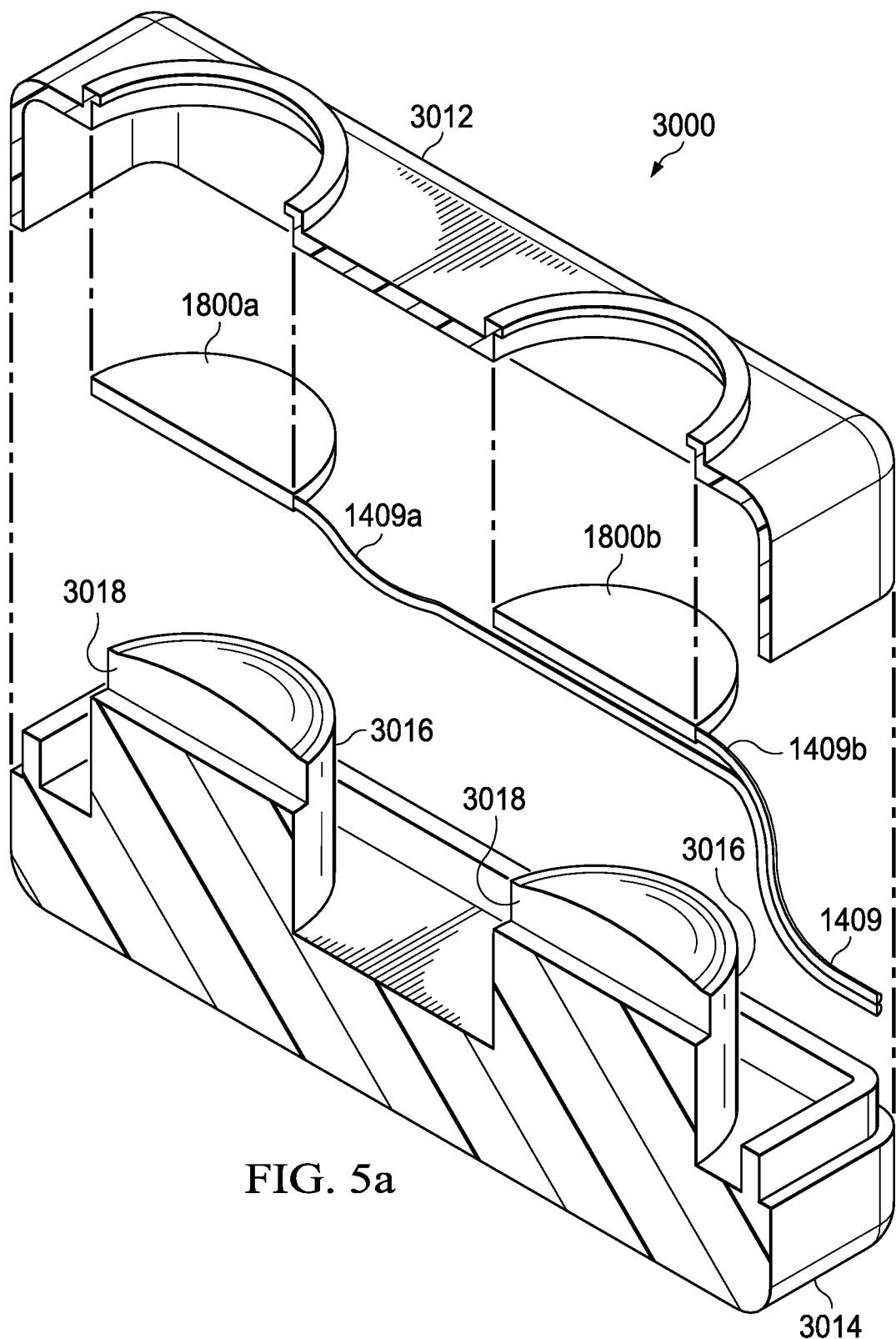
FIG. 5a is an exploded perspective view of the cross-sectional view as similarly shown in FIG. 5.
Figure 5B:
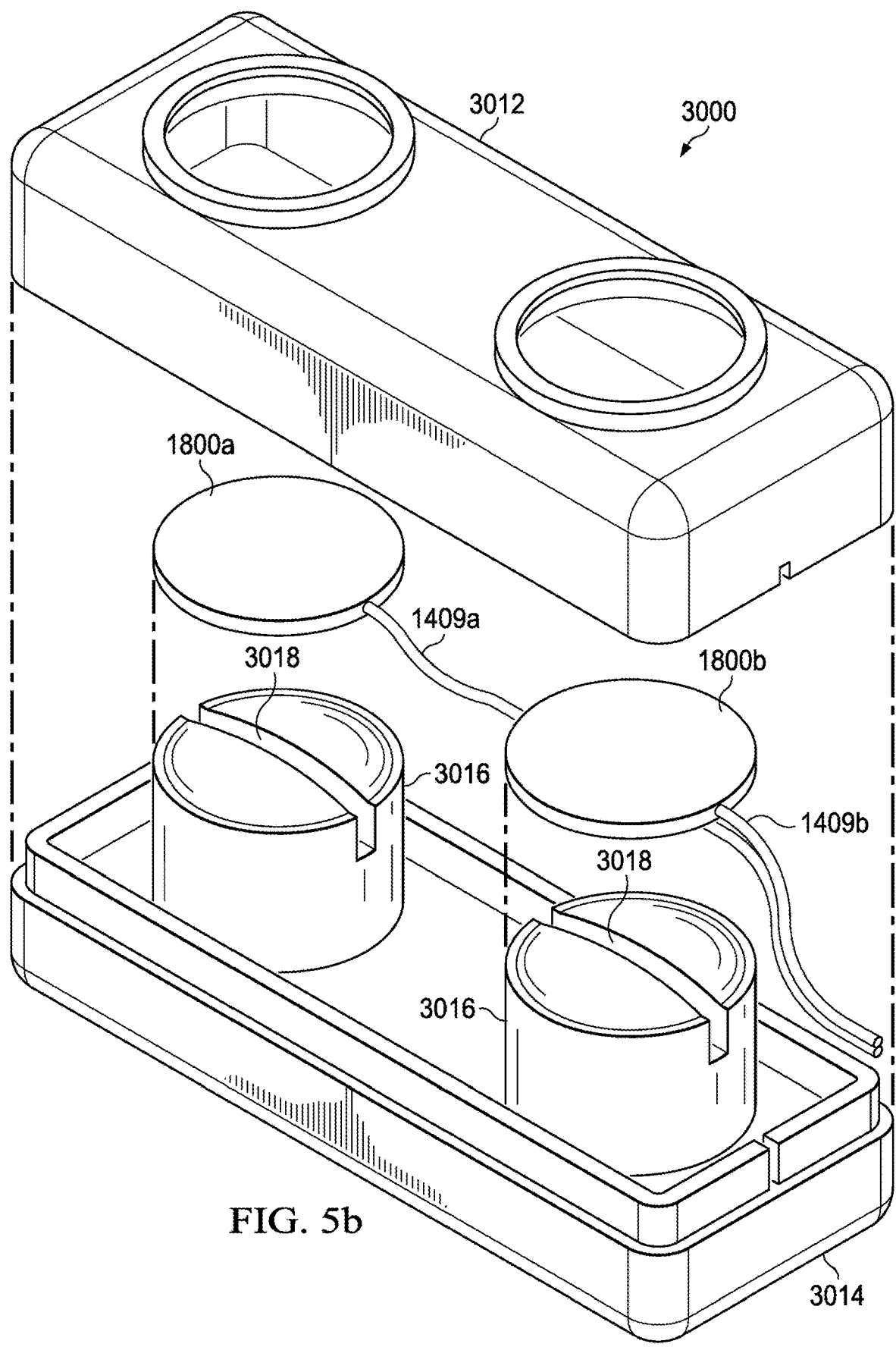
FIG. 5b is an exploded perspective view of an embodiment of a dry elastomer electrode in a bar electrode as similarly shown in FIGS. 3 and 4.
Figure 6:
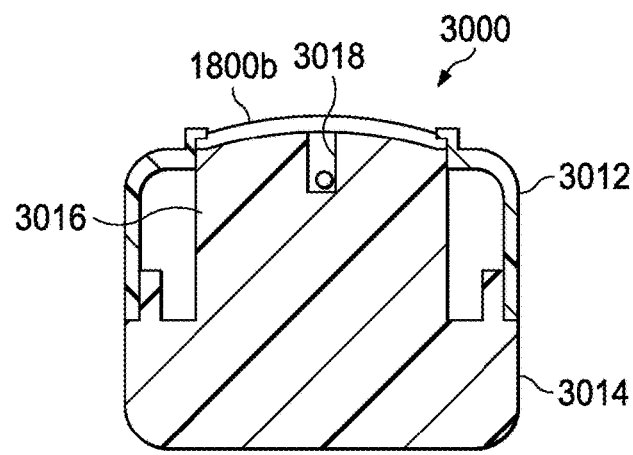
FIG. 6 is a cross-sectional side view taken along line 6-6 of FIG. 3.

FIG. 2 illustrates another embodiment of an electrode 1800 which includes four layers 1401, 1403, 1417 and 1411. The first or top layer 1401 is the interfacing layer and is a silver filled silicone rubber (or elastomer) skin interface. The second layer 1403 is a conductive adhesive layer is positioned in-between first layer 1401 and third layer 1417. The third layer 1417 is an Ag/AgCl film and is positioned between second layer 1403 and fourth layer 1411. The fourth layer 1411 is a dielectric backing layer and is positioned below third layer 1417. An electrical lead 1409 is positioned and secured between the third layer 1417 and the fourth layer 1411. The electrical lead 1409 facilitates the delivery of energy to the electrode 1800 from a power/recording source (not shown).

Though the interfacing or upper layer is described as including the metal integral conductive silicon rubber (or elastomer), other layers may also include the elastomer covering, e.g. conductive inks, or other materials which may facilitate the prevention of corrosion. In addition, one or more other interfacing or upper layers may be added on top of the metal integral conductive silicon rubber (or elastomer) for interfacing with the skin. In another embodiment a plurality of metal integral conductive silicon rubber (or elastomer) layers may be used.

The elastomer is preferably a conductive material with low volume resistivity, such as silicone rubber.

In an embodiment, a dry and flexible electrode is prepared by stacking the desired layers as described herein and pressing them. For the interfacing or top layer 1401, an electrically conductive silicone elastomer containing silver fillers is utilized. Then a pressure is applied to the electrode. The amount of pressure applied to the electrode layers depends upon the desired operating parameters for the electrode for a particular user.

Figure 11:
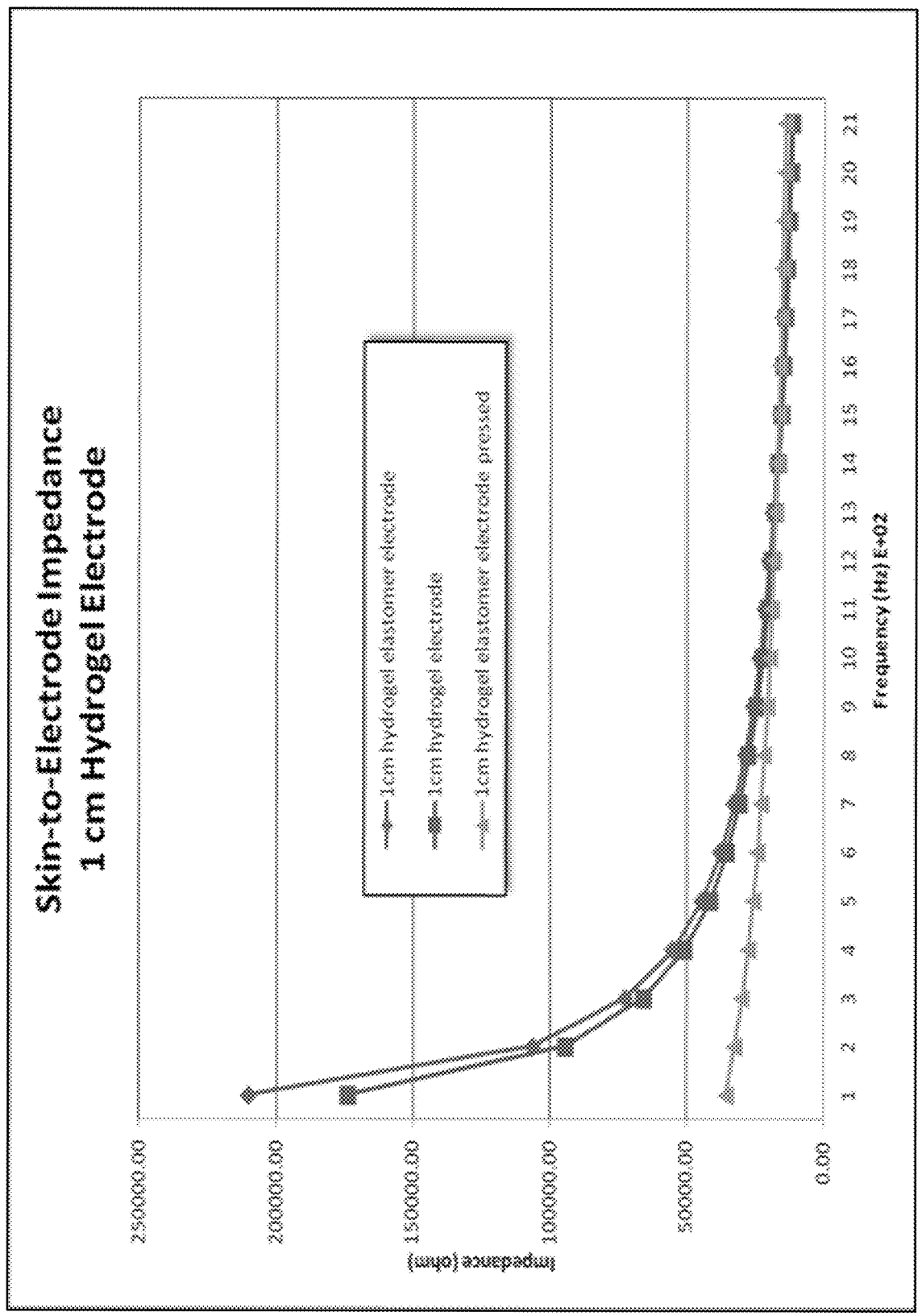
FIG. 11 illustrates a graph of skin to electrode impedance for an embodiment of a Hydrogel Electrode.
Figure 12:
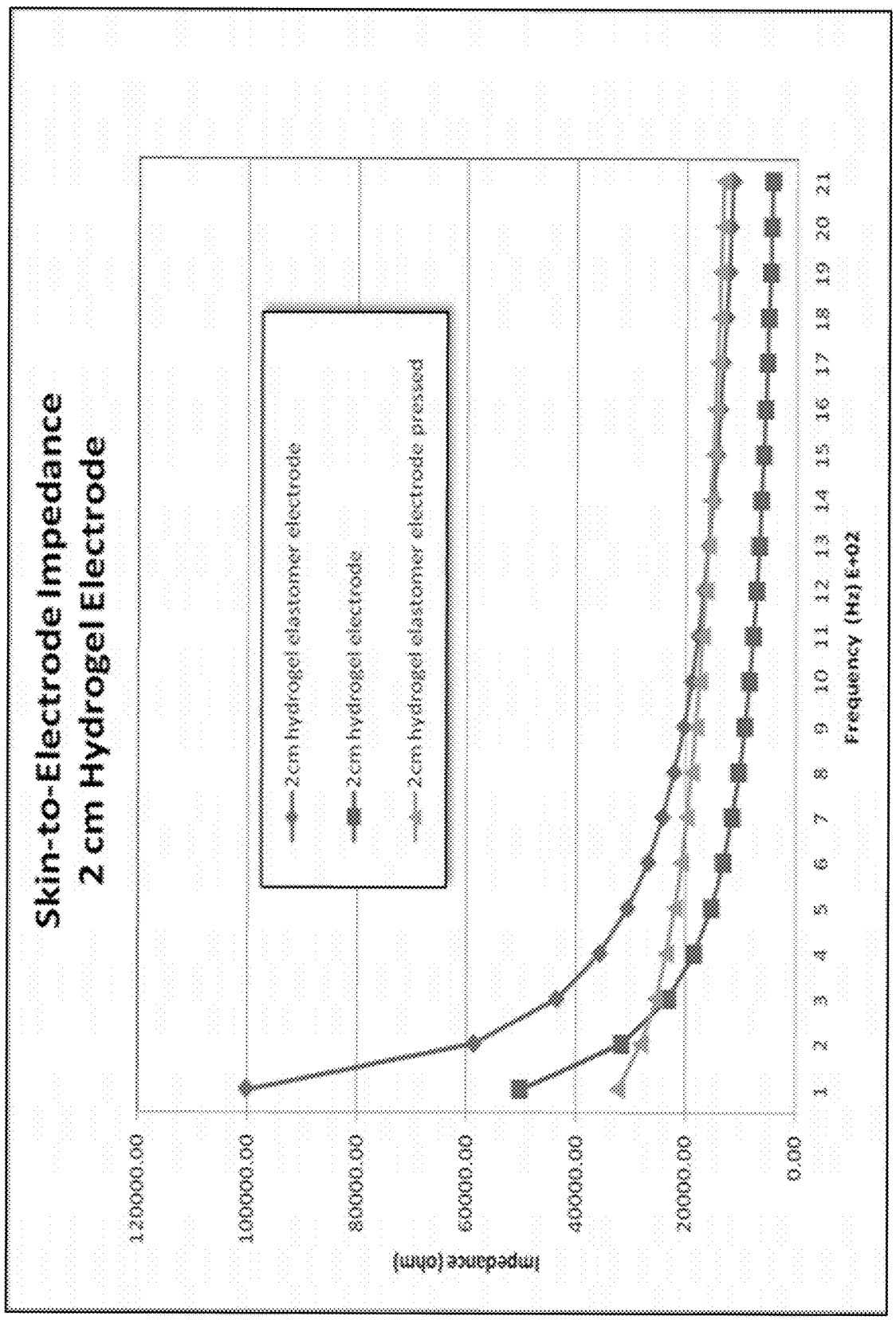
FIG. 12 illustrates a graph of skin to electrode impedance for another embodiment of a Hydrogel Electrode.
Figure 13:
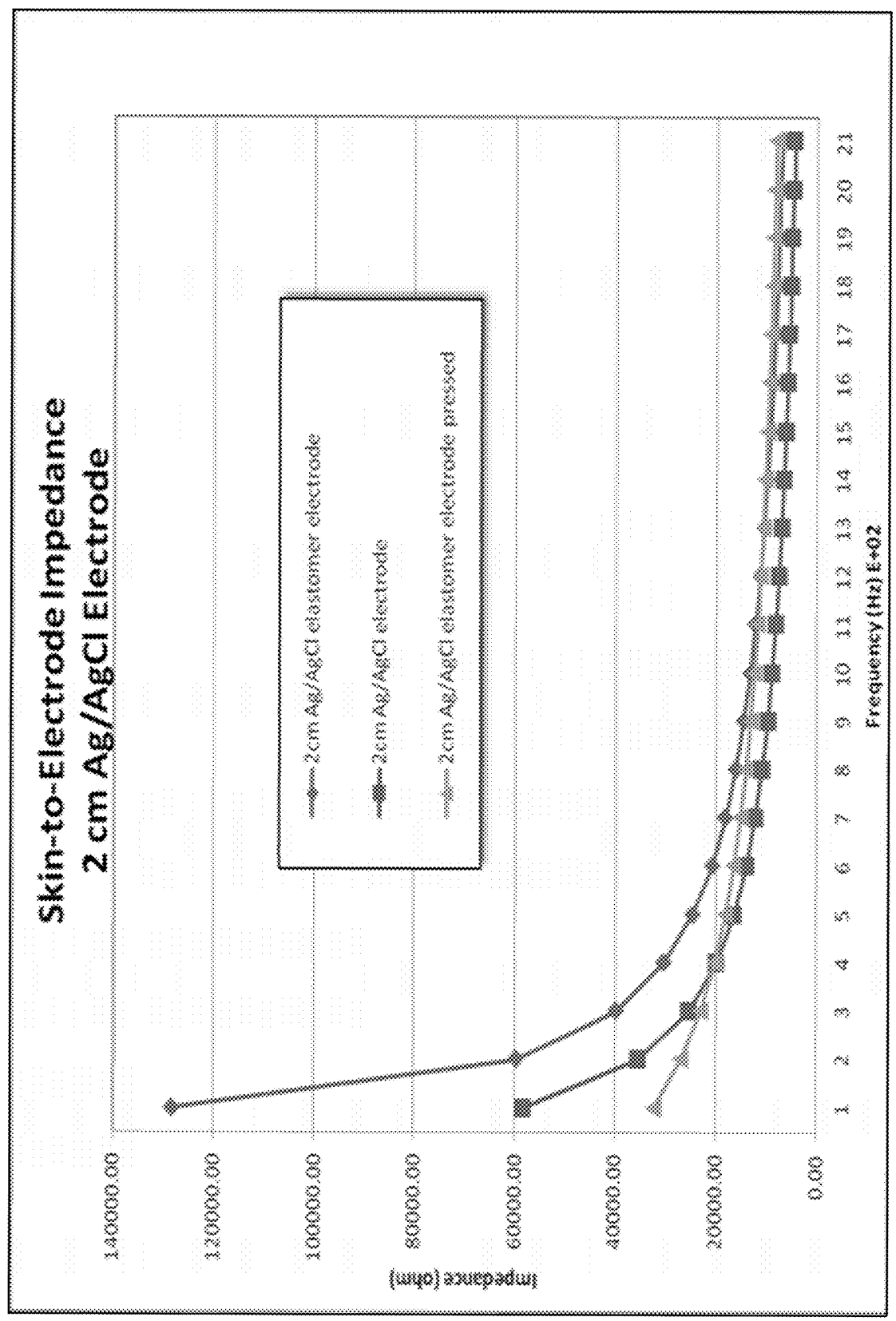
FIG. 13 illustrates a graph of skin to electrode impedance for an embodiment of an Ag/AgCl Electrode.
Figure 14:
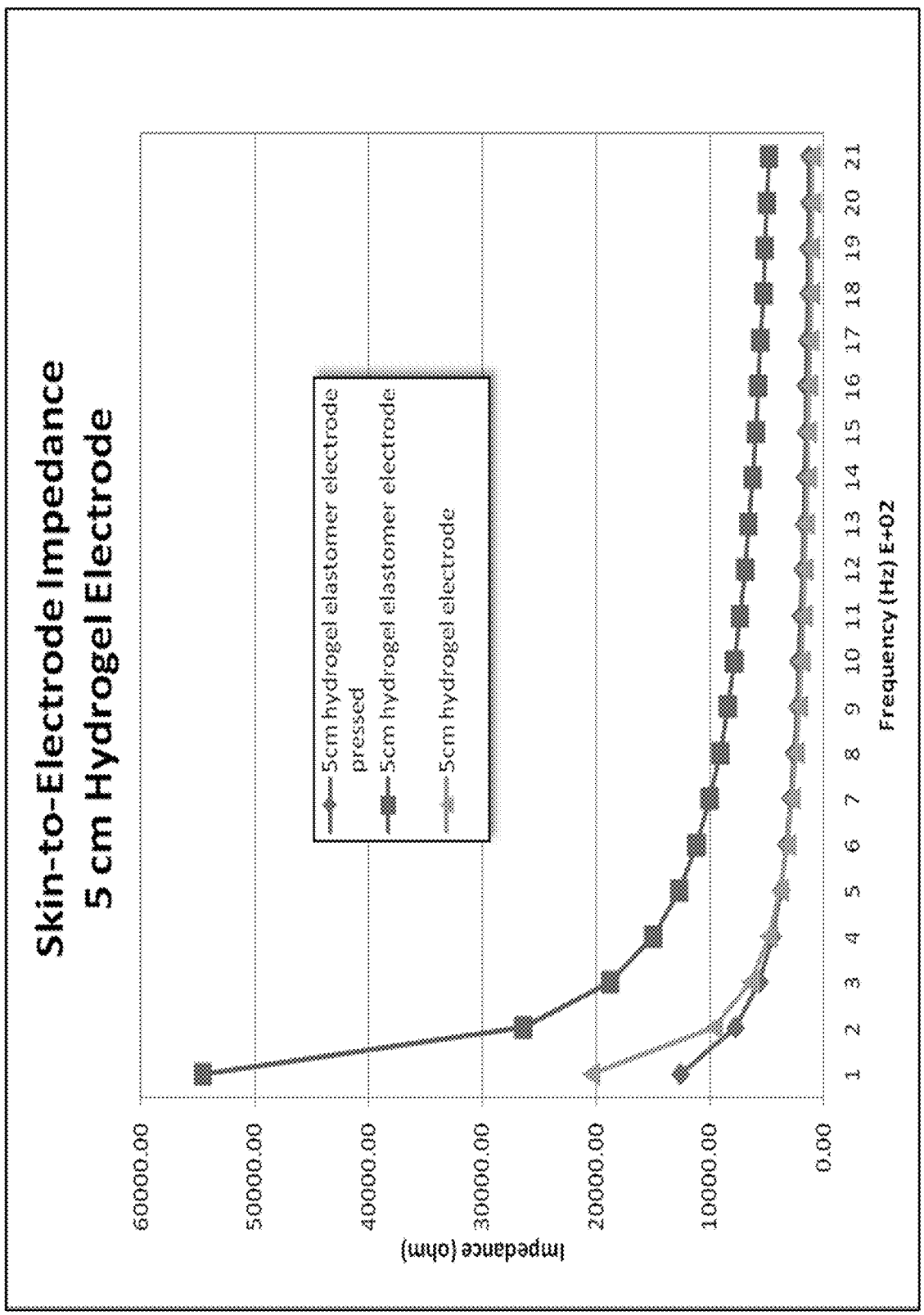
FIG. 14 illustrates a graph of skin to electrode impedance of another embodiment of a Hydrogel Electrode.

FIG. 11 illustrates a graph of skin to electrode impedance for an embodiment of a Hydrogel Electrode. FIG. 12 illustrates a graph of skin to electrode impedance for another embodiment of a Hydrogel Electrode. FIG. 13 illustrates a graph of skin to electrode impedance for an embodiment of an Ag/AgCl Electrode. FIG. 14 illustrates a graph of skin to electrode impedance of another embodiment of a Hydrogel Electrode. For example, in an embodiment, the pressure was approximately 429 PSI for a 5 cm (diameter) electrode and as high as approximately 2684 PSI for a 2 cm electrode and at approximately 11914 PSI for a 1 cm electrode though other pressures may facilitate optimal operation as well, as evidenced by the reduced electrode-skin impedance values. In an embodiment, lower electrode-skin impedance values were found as shown in FIGS. 11-14. FIGS. 11-14 illustrate how compression after laminating changes impedance of elastomer electrodes.

As seen in FIGS. 11-14, different values of impedance are observed, with pressure applied to an electrode, at different frequency ranges. In an embodiment, the pressure applied to an electrode is adjusted during manufacture to try to achieve a certain impedance for a desired frequency range. For example, as shown in FIG. 14, a 5 cm elastomer-hydrogel electrode with pressure applied has a lower impedance than similar hydrogel electrode, only at lower frequencies, and a much lower impedance than elastomer-hydrogel electrode that has been laminated but not pressed, across the entire frequency range. Similarly, as shown in FIG. 11, for a 1 cm elastomer-hydrogel electrode operating at a lower frequency range, more pressure may be applied during manufacture to the elastomer-hydrogel electrode to obtain a lower impedance value for that frequency range while less pressure is applied to a 1 cm elastomer-hydrogel electrode that is operating in a higher frequency range. Thus, pressure applied during manufacturing of an electrode is adjusted to attempt to optimize performance of the electrode at a required or desired frequency value.

In an embodiment, to mitigate the "edge effect" and to provide even current density distribution across the electrode, a given electrode is pressed concentrically, where increasingly higher force is applied from the periphery toward the center of the electrode, and thus creating a "segmented impedance" electrode or a varying impedance electrode with the higher impedance at the periphery of the electrode and the lowest resistance in the center of the electrode. For example with an electrode having at least 2.5 cm radius, the following could be utilized to create a "segmented impedance" electrode:

i. 2.5 cm radius is pressed with 500 PSI, then
    ii. 2.0 cm radius is pressed with 2000 PSI, then
    iii. 1.5 cm radius is pressed with 4000 PSI, then
    iv. 1.0 cm radius is pressed with 8000 PSI, then
    v. 0.5 cm radius is pressed with 12000 PSI.

Other radii and/or pressures applied to the electrode may be implemented in addition to or alternatively to those shown above. In an embodiment, the electrode has the physical structure of the electrode described herein. In another embodiment, the concentrically applied pressure may be used with an electrode having similar or other physical structures and shapes as well.

Although illustrated hereinabove in the various embodiments as circular shaped electrodes, it is contemplated that the claims are not limited to circular shaped electrodes, rather the electrodes of the claims could be of virtually any shape and size with the applied pressure varying from the outer most perimeter to the middle portions so as to provide a selected performance for a particular user.

FIGS. 3-10 illustrate various embodiments of form factors for use of the multilayered dry elastomer electrode as described herein above with respect to FIGS. 1a, 1b, 1c, and 2. Although FIGS. 3-10 are illustrated with a single embodiment of the electrode, it is contemplated that any of the electrode embodiments described herein could be utilized and be within the scope of the claims. It is further contemplated to be within the scope of the claims that other form factors and embodiments may also employ the multilayered dry elastomer electrode.

Referring now to FIGS. 3-6, there is illustrated an embodiment of a bipolar stimulator bar electrode 3000 utilizing multilayered dry elastomer electrodes described hereinabove. Typically bar electrodes are attachable to a stimulator device or electromyographic (EMG) device (not shown) and are utilized for skin or surface stimulation of peripheral nerves. It can be configured with to perform both as a stimulation electrode and a recording electrode, to record nerve and muscle action potentials and to provide electrical stimulation.

Bar electrode 3000 includes an elongated body 3010 having a top 3012 and a bottom 3014. Two cylindrical shape posts 3016 having convex upper surfaces extend up from bottom 3014. Each of posts 3016 have a slot 3018 extending there-across. An electrode, such as described herein above, 1800a and 1800b are placed across the top surfaces of posts 3016 and are positioned between top 3012 and bottom 3014. Electrodes 1800a and 1800b conform to the convex shape of the top surfaces of posts 3016. Holes in top 3012 that are positioned in alignment of posts 3016 in top 3012 permit at least a portion of the electrodes 1800a and 1800b to extend above top 3012 (see FIGS. 4 and 5).

The slots 3018 of each of the posts 3016 are configured in shape to receive the leads 1409a and 1409b of electrodes 1800a and 1800b, respectively. This facilitates the leads 1409 to extend from the bar electrode and ultimately be connected to the stimulator device (not shown).

Figure 7:
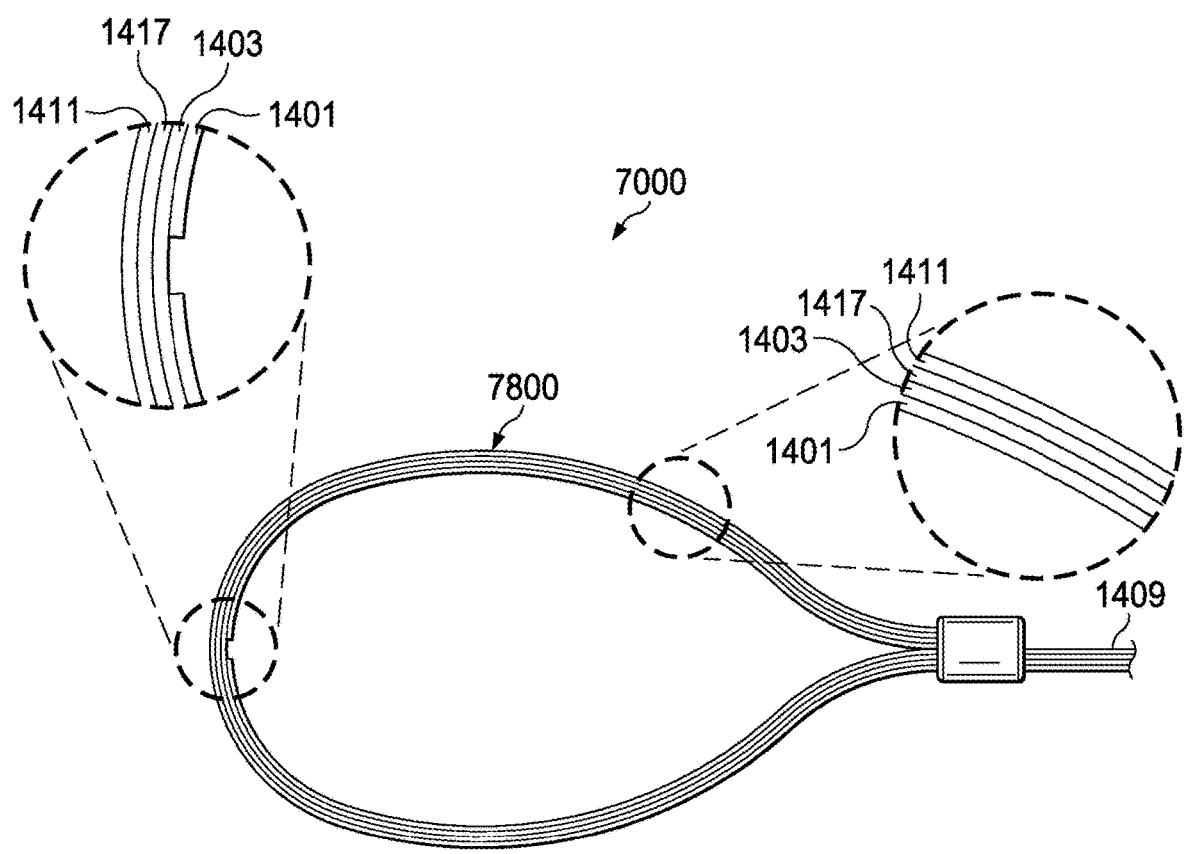
FIG. 7 is a top view of a digital ring electrode with portions enlarged.
Figure 8:
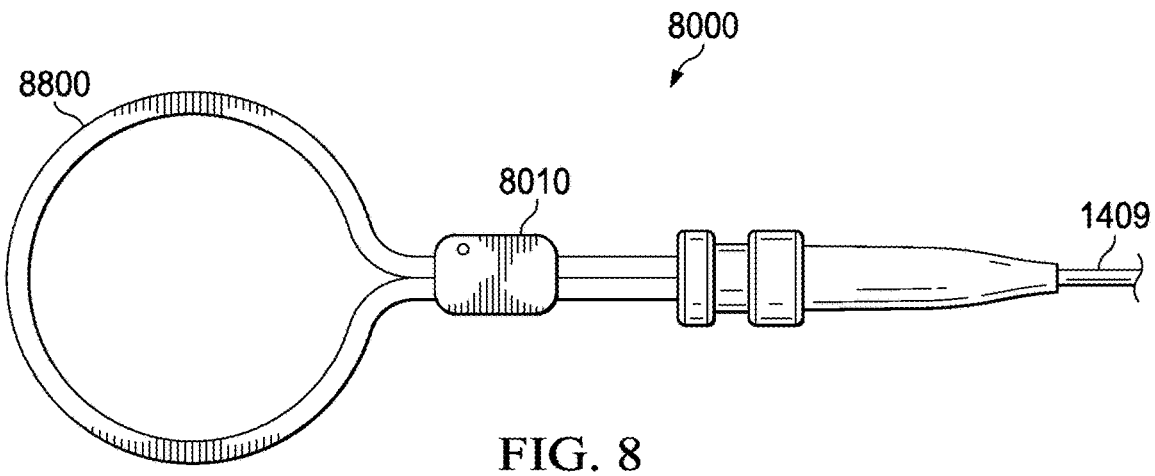
FIG. 8 is a top view of an another embodiment of a digital ring electrode with a clip.
Figure 8A:
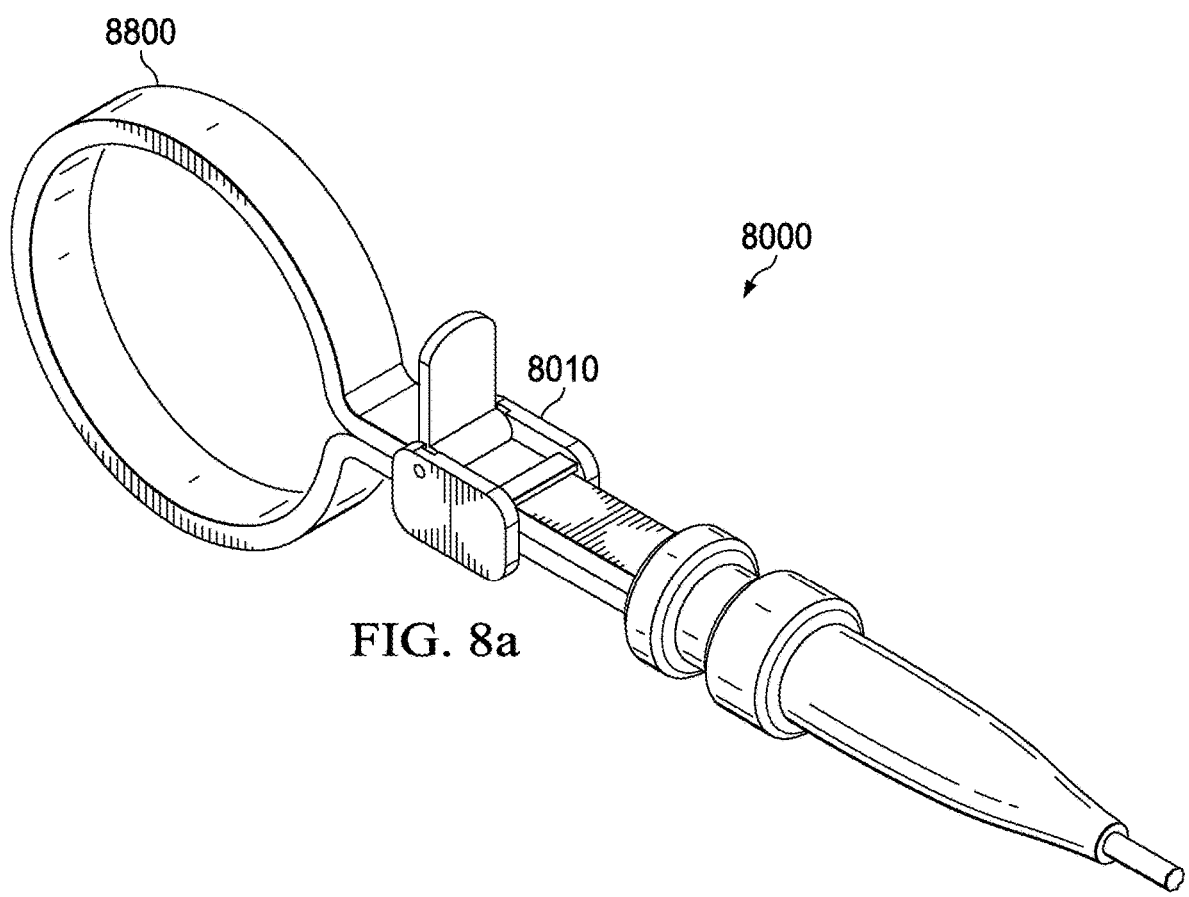
FIG. 8a is a perspective view of a digital ring electrode with a clip as similarly shown in FIG. 8 with the clip in an open position.
Figure 8B:
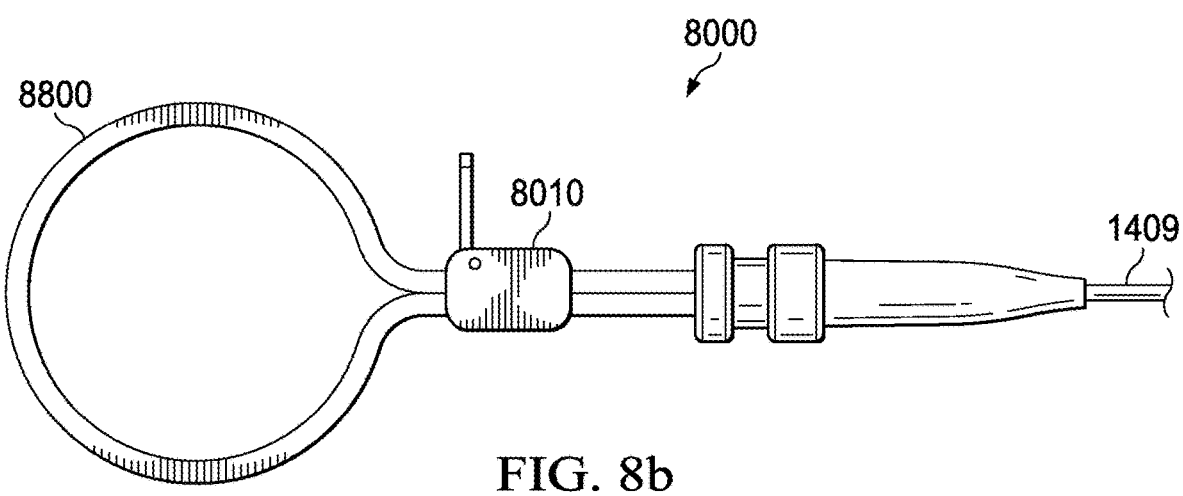
Figure 8C:
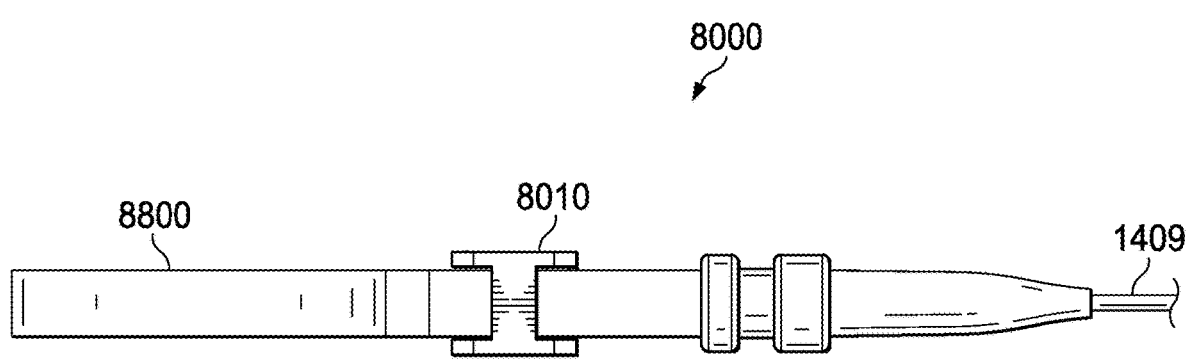
FIG. 8c is a side view of the digital ring electrode as similarly shown in FIG. 8.

Referring now to FIGS. 7-8c, there are illustrated examples of digital ring electrodes employing multilayered dry elastomer electrodes in accordance with the principles of the claims as described herein. It is contemplated that the embodiments of the digital ring electrodes illustrated in FIGS. 7-8c may be the same with the exception that the embodiment disclosed in FIG. 8 may employ a clip or cord lock as discussed in more detail herein below. As can be appreciated, digital ring electrodes are often used for sensory nerve stimulation or recording from the fingers and toes of patients.

Referring now to FIG. 7, there is illustrated an embodiment of noose type digital ring electrodes 7000. The ring electrode portion 7800 is a multilayered dry elastomer electrode as similarly described herein, with the inner most layer 1401 being silver filled silicone rubber. The next layer 1403 is a conductive adhesive layer, while the third layer 1417 is an Ag/AgCl film, while the outer layer 1411 is a dielectric backing layer. Layer 1401 has a gap or plurality of gaps preventing delaminating while adjusting either the radius or diameter to the given size.

Referring now to FIGS. 8, 8a, 8b and 8c, there is illustrated another embodiment of another digital ring electrode 8000. The ring electrode portion 8800 is a multilayered dry elastomer electrode as described in the various electrode embodiments herein. Digital ring electrode 8000 includes a clip 8010 (or cord lock—not shown) which facilitates the adjustment of the size of the electrode portion 8800. When in the clip 8010 (or cord lock—not shown) is in the open position (FIGS. 8a and 8b), the inner diameter of the electrode 8800 can be adjusted to facilitate the placement of the electrode 8800 onto a finger or toe of a patient and then adjusted to the proper size to secure the electrode 8800 in place. When clip 8010 (or cord lock—not shown) is in the closed position (FIG. 8), the size of the inner diameter of the electrode 8800 cannot be adjusted, thereby keeping the electrode 8800 in place the testing of the patient.

Figure 9:
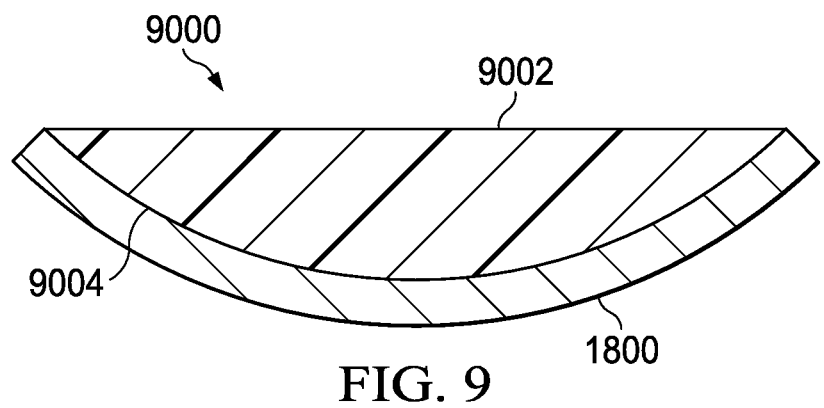
FIG. 9 is a partial cross-sectional view of an electrode with a disc as a backing layer where the electrode conforms to the convex shape of the disc.
Figure 10:
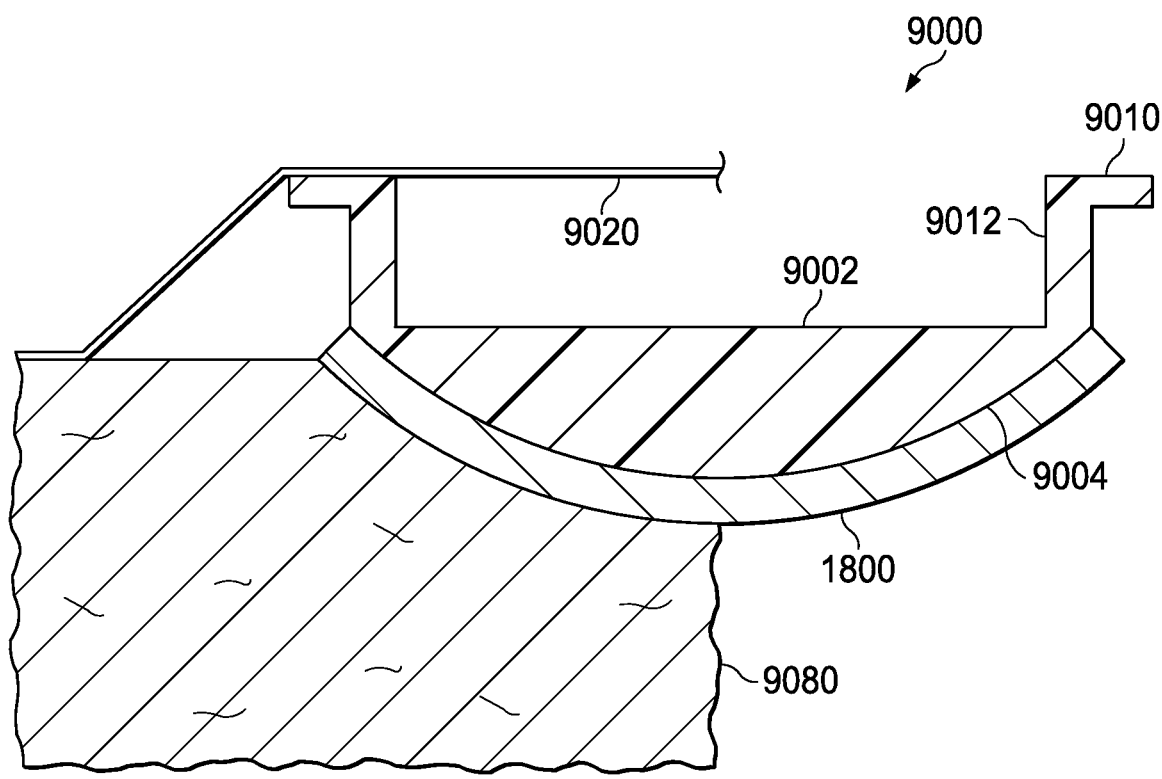
FIG. 10 is a partial cross-sectional view of an electrode with a disc as a backing layer where the electrode conforms to the convex shape of the disc providing uniform contact with the skin.

Referring now to FIGS. 9 and 10, there is illustrated an embodiment of disc electrode 9000 employing multilayered electrodes in accordance with the principles as described herein, such as, but not limited to electrode 1400, 1600, and 1800. As illustrated disc electrode 9000 includes a disc 9002 having a convex outer surface 9004, a cylindrical wall 9012 and a flange 9010. An electrode 1800 is attached to the convex surface 9004 of disc 9002 for placement providing uniform contact against the patient's skin 9080. An adhesive 9020 can be utilized to secure the disc electrode 9000 to the patient during use.

The specification has described, at least in part, one or more embodiments. The one or more embodiments described are used herein, an aspect thereof, a feature thereof, a concept thereof, and/or an example thereof. A physical embodiment of an apparatus, an article of manufacture, a machine, and/or of a process that embodies the aspects described herein may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While particular combinations of various functions and features have been expressly described herein, other combinations of these features and functions are likewise possible. The claims are not limited by the particular examples disclosed herein and expressly incorporates these other combinations.

What is claimed is:

1. A method for manufacturing a varying impedance electrode, comprising:
   compressing a metal integral conductive silicone rubber material layer with a first compression force at the perimeter during manufacture; and
   compressing the metal integral conductive silicone rubber material layer with a second, different compression force at the center during manufacture; and
   stacking a plurality of layers, wherein a first layer includes the metal integral conductive silicone rubber material layer and a second layer includes a dielectric material layer.

2. The method of claim 1, further comprising:
positioning a conductive lead intermediate the metal integral conductive silicone rubber material layer and the dielectric material layer.

3. The method of claim 1, wherein the first compression force at the perimeter is less than the second compression force at the center.

4. The method of claim 1, wherein the metal integral conductive silicone rubber material layer is configured for positioning most proximate to a patient to conduct an electrical stimulation signal to the patient.

5. The method of claim 4, further comprising:
positioning a conductive lead intermediate the metal integral conductive silicone rubber material layer and the dielectric material layer of the varying impedance electrode, wherein the conductive lead is configured for connection to a stimulation device for receiving the electrical stimulation signal.

6. The method of claim 1, wherein compressing the metal integral conductive silicone rubber material layer with the second, different compression force at the center creates an impedance at the perimeter greater than the impedance at the center of the electrode.

7. The method of claim 6, wherein the first compression force at the perimeter is less than the second, different compression force at the center.

8. The method of claim 1, further comprising:
positioning a third layer in the plurality of layers intermediate the metal integral conductive silicone rubber material layer and the dielectric material layer, wherein the third layer includes a conductive gel material.

9. The method of claim 1, further comprising:
positioning a second electrode and the varying impedance electrode in a bar electrode configuration.

10. The method of claim 1, wherein the varying impedance electrode is a dry electrode.

11. The method of claim 10, wherein the metal integral conductive silicone rubber material layer is configured for positioning most proximate to the patient.

12. The method of claim 1, wherein:
compressing the metal integral conductive silicone rubber material layer with the first compression force at the perimeter generates a first impedance in the periphery of the electrode during manufacture; and
compressing the metal integral conductive silicone rubber material layer with the second, different compression force at the center generates a second lower impedance in the center of the electrode during manufacture.

13. A method for manufacturing a varying impedance electrode, comprising:
stacking a plurality of layers, with a first of the layers comprising a metal integral conductive silicone rubber material and a second of the layers comprising a dielectric material;
compressing the plurality of stacked layers with a first compression force at the perimeter of the plurality of layers during manufacture, wherein the perimeter has a first impedance; and
compressing the plurality of stacked layers with a second, different, force at the center of the plurality of layers during manufacture, wherein the center has a second, different impedance.

14. The method of claim 13, wherein the first impedance at the perimeter of the electrode is greater than the second, different impedance at the center of the electrode.

15. The method of claim 13, wherein the first force at the perimeter is less than the compression force at the center.

16. The method of claim 13, further comprising:
positioning a third layer in the plurality of layers intermediate the first and second layer, wherein the third layer includes a conductive gel material.

17. The method of claim 13, further comprising:
compressing the plurality of stacked layers concentrically, wherein increasingly higher force is applied from the periphery toward the center of the plurality of stacked layers.

18. A method for manufacturing a varying impedance electrode, comprising:
compressing a center of a metal integral conductive silicone rubber material with a first compression force during manufacture to obtain a first impedance at the center; and
compressing the perimeter of the metal integral conductive silicone rubber material with a second, different compression force during manufacture to obtain a second, different impedance at the perimeter; and
stacking a plurality of layers to form the varying impedance electrode, with a first of the plurality of layers including the metal integral conductive silicone rubber material and a second of the plurality of layers including a dielectric material.

19. The method of claim 18, wherein the first compression force is greater than the second, different compression force.

20. The method of claim 18, wherein the wherein the first impedance at the center is less than the second, different impedance at the perimeter.

* * * * *